US007393943B1

(12) United States Patent
Ni et al.

(10) Patent No.: US 7,393,943 B1
(45) Date of Patent: Jul. 1, 2008

(54) POLYNUCLEOTIDES ENCODING A HUMAN CHEMOTACTIC CYTOKINE I

(75) Inventors: Jian Ni, Rockville, MD (US);
Guo-Liang Yu, Darnestown, MD (US);
Pedro Alfonso, Gaithersburg, MD (US);
Reiner Gentz, Silver Springs, MD (US);
Jeffrey Y. Su, Gaithersburg, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 302 days.

(21) Appl. No.: 08/761,289

(22) Filed: Dec. 6, 1996

Related U.S. Application Data

(60) Provisional application No. 60/008,387, filed on Dec. 8, 1995.

(51) Int. Cl.
*C07H 21/04* (2006.01)
*C12P 21/06* (2006.01)
*C12N 1/20* (2006.01)
*C12N 15/00* (2006.01)
*C12N 5/00* (2006.01)
*C12N 5/02* (2006.01)
*C12N 15/74* (2006.01)

(52) U.S. Cl. .................. 536/23.5; 435/69.1; 435/252.3; 435/320.1; 435/325; 435/471

(58) Field of Classification Search ................ 536/23.5, 536/24.33; 435/69.5, 252.3, 320.1
See application file for complete search history.

(56) References Cited

U.S. PATENT DOCUMENTS 5,350,836 A * 9/1994 Kopchick et al.
5,504,003 A 4/1996 Li et al.
5,525,486 A 6/1996 Honjo et al.
5,976,832 A * 11/1999 Hitomi et al.

FOREIGN PATENT DOCUMENTS

EP 731166 A2 9/1996

OTHER PUBLICATIONS

Vukicevic et al. PNAS USA 93:9021-9026, 1996.*
Massague J. Cell 49:437-8, 1987.*
Pilbeam et al. Bone 14:717-720, 1993.*
Skolnick et al. Trends in Biotech. 18:34-39, 2000.*
Bork P. Genome Research 10:398-400, 2000.*
Doerks et al. Trends in Genetics 14:248-250, 1998.*
Smith et al. Nature Biotechnology 15:1222-1223, 1997.*
Brenner SE. Trends in Genetics 15:132-133, 1999.*
Bork et al. Trends in Genetics 12:425-427, 1996.*
DDBJ/GenBank Database, Natl. Cancer Center Res. Inst., Growth Factor Div. (Tokyo, Japan), No. D49549, Calcium-binding protein in amniotic fluid, Mar. 9, 1995, see sequence alignment.
DDBJ/EMBL/GenBank Databse, Natl. Cancer Center Res. Inst., Growth Factor Div. (Tokyo, Japan), No. 49548, Bovine mRNA calcium-binding protein in amnioic fluid, Mar. 9, 1995, see sequence alignment.
EST-STS Database, WashU-Merck EST Project (St. Louis, MO., USA) No. R02722, Hillier et al. "ye76a09.slzHomo sapiens cDNA clone 123640 3' similar to SP:CAGC-PIG P80310 Calgranulin C'", Mar. 31, 1995, see sequence alignment.
EST-STS Database, WashU-Merck EST Project (St. Louis, MO., USA) No. R02721, Hillier et al. "ye76a09.rl Homo sapiens cDNA clone 123640 5' similar to SP:CACG-PIG P80310 Calgranulin C'", Mar. 31, 1995, see sequence alignment.
GenSeq Accession No. T39345 (May 1, 1997).
GenSeq Accession No. T39346 (May 1, 1997).
GenSeq Accession No. W03564 (May 1, 1997).
Howard et al., Trend. Biotechnol. 14:46-51 (1996).
Wells et al., J. Leukocyte Biol., 59: 53-60 (1996).
Horuk et al., J. Lukeocyte Biol., 59:29-38 (1996).
Szabo et al., J. Biol. Chem., 270:25348-25351 (1995).
Proost et al., Biochemistry 32:10170-10177 (1993).
Liao et al., J. Exp. Med., 182:1301-1314 (1995).
Schulz-Knappe et al., J. Exp. Med., 183:295-299 (1996).
Luo et al., J. Immunol., 153:4616-4624 (1994).
Proudfoot et al., J. Biol. Chem., 271:2599-2603 (1996).
Gong et al., J. Biol Chem., 271:10521-10527 (1996).
Hara et al., J. Immunol., 155:5352-5358 (1995).
Newton R.A. and Hogg, N. "The Human S100 Protein MRP-14 is a Novel Activator of the $\beta_2$ Integrin Mac-1 on Neutrophils," J. Immunology 160(3):1427-1435 (1998).
GenBank Accession No. BAA08497, Feb. 10, 1999.
GenBank Accession No. D83657, Feb. 6, 1999.
GenBank Accession No. D83664, Feb. 6, 1999.
GenBank Accession No. X98289, Aug. 11, 1997.

(Continued)

Primary Examiner—Robert Landsman

(57) ABSTRACT

Human chemotactic cytokine I polypeptides and DNA (RNA) encoding such chemotactic cytokines and a procedure for producing such polypeptides by recombinant techniques is disclosed. Also disclosed are methods for utilizing such chemotactic cytokines for the treatment of leukemia, tumors, chronic infections, auto-immune disease, fibrotic disorders, wound healing and psoriasis. Antagonists against such chemotactic cytokines and their use as a therapeutic to treat rheumatoid arthritis, auto-immune and chronic and acute inflammatory and infective diseases, allergic reactions, prostaglandin-independent fever and bone marrow failure are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding the chemotactic cytokines and for detecting altered levels of the polypeptide in a host.

34 Claims, 3 Drawing Sheets

OTHER PUBLICATIONS

GenBank Accession No. X98290, Aug. 11, 1997.
GenBank Accession No. X97859, Jul. 14, 1997.
GenBank Accession No. AA313230, Apr. 19, 1997.
GenBank Accession No. AA321239, Apr. 19, 1997.
Genbank Accession No. AA203475, Jan. 24, 1997.
GenBank Accession No. W65311, Oct. 15, 1996.
GenBank Accession No. W65341, Oct. 15, 1996.
GenBank Accession No. U13666, Apr. 1, 1995.
Bush, K et al., Clin. Exp. Immunol (2001) vol. 123:487-495.
Dell'Angelica, E. et al., J. Biol. Chem. (1994) vol. 269:28929-28936.
Devery, J. et al., J. Immunol. (1994) vol. 152:1888-1897.
Guignard, F. et al., Biochem. Journal (1995), vol. 309:395-401.
Hessian, P. et al., J. Leukocyte Biol. (1993) vol. 53:197-204.
Iismaa, S. et al., DNA & Cell Biol. (1994) vol. 13:183-192.
Ilg, E. et al., Bioch. & Bioph.Research Comm. (1996) No. 225:146-150.
Johnston, B. et al., The J. of Immunology, (1997) vol. 159:4514-4523.
Lackmann, M. et al., J. Biol. Chem. (1992) vol. 267:7499-7504.
Lackmann, M. et al., J. Immonol. (1993) vol. 150:2981-2991.
Lagasse, E., et al., Mol. & Cell Biol. (1988) vol. 8:2402.
Lau, W., et al., J. Clin. Invest. (1995) vol. 95:1957-1965.
Marti, T. et al., Bioch. & Bioph.Research Comm., (1996) vol. 221:454-458.
Miranda, L. et al., FEBS Letters (2001), vol. 288:85-90.
Schafer, B et al., Genomics (1995), vol. 638-643.
Watanabe, T. et al., Int'l J. of Cardiology, (1996), S51-SA60.
Wicki, R., et al., Cell Calcium (1996), vol. 20(6):459-464.
Yamammura, T et al., Bioch. & Bioph.Research Comm., (1996), vol. 221:356-360.

* cited by examiner

FIG. 1

```
         10                        30                        50
CACGAGCACCACTGCTGGCTTTTTGCTGTAGTCCCACATTCCTGTGTCATTGAGGGGTTAA
         70                        90                        110
CATTAGGCTGTGGGAAGATGACAAAACTTGAAGAGCATCTGGAGGGAATTGTCAATATCTTC
                  M  T  K  L  E  E  H  L  E  G  I  V  N  I  F
         130                       150                       170
CACCAATACTCAGTTCGGAAGGGGCATTTTGACACCCTCTCTAAGGGTGAGCTGAAGCAG
 H  Q  Y  S  V  R  K  G  H  F  D  T  L  S  K  G  E  L  K  Q
         190                       210                       230
CTGCTTACAAAGGAGCTTGCAAACATCAAGAATATCAAAGATAAAGCTGTCATTGAT
 L  L  T  K  E  L  A  N  I  K  N  I  K  D  K  A  V  I  D
         250                       270                       290
GAAATATTCCAAGGCCTGGATGCTAATCAAGATGAACAGGTCGACTTTCAAGAATTCATA
 E  I  F  Q  G  L  D  A  N  Q  D  E  Q  V  D  F  Q  E  F  I
         310                       330                       350
TCCCTGGTAGCCATTGCGCTGAAGGCTGCCATTACCACCACAAAGAGTAGGTAGCT
 S  L  V  A  I  A  L  K  A  A  H  Y  H  T  H  K  E  *
         370                       390                       410
CTCTGAAGGCTTTTTACCCAGCAATGTCCTCAATGGAGGGGTCTTTTCTTTGCCTCACCA
         430                       450                       470
AAACCCAGCTTGACCCCTGGGGGAGTTAAGAGTTAATAACCACACTTACGGAAAGTTCT
```

FIG. 2

```
     1 MTKLEEHLEGIVNIFHQYSVRKGHFDTLSKGELKQLLTKELANTIKNIKD 50
       ::  ::|| ||| :|:|||| ||| || : :|| |: :  : :| |:|
     1 .tkledhlegiinifhqysvrlghydtlikrelkqlitkelpntlkntkd 49

51 KAVIDEIFQGLDANQDEQVDFQEFISLVAIALKAAHYHTHKE 92
       ::|:|:|||| ||::|||| | |: ::|| | | :::|:||
    50 ggtidkifqnldanqdeqvsfkefvvlvtdvlitahdnihke 91
```

POLYNUCLEOTIDES ENCODING A HUMAN CHEMOTACTIC CYTOKINE I

This application claims benefit of priority under 35 U.S.C. § 119(e) to U.S. Provisional Patent Application Ser. No. 60/008,387, filed Dec. 8, 1995.

BACKGROUND OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human chemotactic cytokine I polypeptides. The invention also relates to inhibiting the action of such polypeptides.

The cytokine family of proteins exhibits a wide variety of functions. A hallmark feature is their ability to elicit chemotactic migration of distinct cell types, including polymorphonuclear cells and macrophages. Many cytokines have proinflammatory activity and are involved in multiple steps during inflammatory reactions. In addition to their involvement in inflammation, cytokines have been shown to exhibit other activities. For example, interleukin-8 (IL-8) promotes proliferation of keratinocytes.

In light of the diverse biological activities, it is not surprising that cytokines have been implicated in a number of physiological and disease conditions, including lymphocyte trafficking, wound healing, hematopoietic regulation and immunological disorders such as allergy, asthma and arthritis.

The S100 family of calcium binding proteins has chemotactic activity for polymorphonuclear cells, mononuclear cells and neutrophils and are calcium binding proteins. The S100 protein has been recently identified in cells of myeloid origin and consists of macrophage inhibitory factor-related protein (MRP-8), MRP-14, chemotactic protein 10 (CP-10) and calgranulin C.

MRP-8 and MRP-14 belong to the S100 family of proteins, which includes calbindin, and calcyclin (Kligman, D. and Hilt, D. C., *Trends Biochem. Sci.*, 13:437-443 (1998)). This group of protein ranges in molecular size from 10 to 14 kd and are also expressed in a cell lineage-specific manner. Alignment of individual sequences shows that there is overall conservation of structure within the family, a notable feature being the two calcium binding sites, which are the "EF hand" type. Sequences at both the $NH_2$- and COOH-terminal ends of MRP-8 and MRP-14 are relatively hydrophobic. An attractive hypothesis is that these regions of the molecule are buried until calcium binding brings about the conformational changes that cause their exposure, making them potentially available for interactions with other effector molecules. Because of the extended sequence of its COOH-terminal "tail" MRP-14 is the largest member of the S100 family. (Hessian, P., et al., *J. Leuk. Bio.*, 53:197-204 (1993).

Each gene in the S100 family is composed of three exons with one intron interrupting the protein-coding sequence between the two EF hands. The MRP-8 and MRP-14 genes are both localized to chromosome 1Q12-Q21 with an undefined distance between them (Dorin J. R., et al., *Nature*, 326:614-617 (1987) and Lagasse, E. and Clerc, R. G., *Mol. Cell. Biol.*, 8:2402, 2410 (1988)). Two other S100 family members 1882 (CAPL) and calcyclin/2A9 (CACY) also map to chromosome 1Q12-Q21 (Dorian, J. R., et al., *Genomics*, 8:420-426 (1990). It is probably that co-segregation of these five genes on chromosome 1 may represent an S100 family locus. However, this does not apply to all S100 homologs.

MRP-8 and MRP-14 are restricted to cells of the monocytes/macrophage lineage, neutrophils, and under certain circumstance keratinocytes, suggesting that its expression is tightly regulated during differentiation (Hogg, N., et al., *Eur. J. Immunol.*, 19:1053-1061 (1989)). Thus, monocytes and neutrophils in the circulation express MRP-8 and MRP-14, in contrast to other related cells such as lymphocytes, platelets, basophils and eocynophils which do not (Id.).

Resident tissue macrophages do not express MRP-8 and MRP-14, implying that differentiation of monocytes to macrophages is normally associated with loss of this molecule (Id.). Furthermore, immunohistochemical data show that at inflammatory sites MRP-8 and MRP-14 positive cells are associated with vessels but that the majority of monocytes already within the tissues at these sites have lost MRP-8 and MRP-14 expression (Id.). In keeping with these observations, tissue culture-matured monocytes down regulate this molecule (Zwadlo, G., et al., *Clin. Exp. Immunol.*, 72:510-515 (1988)).

At sites of chronic inflammation in patients with diseases such as rheumatoid arthritis, sarcoidosis, tuberculosis or onchocerciasis macrophages express both MRP-8 and MRP-14 (Palmer, D. G., et al., *Clin. Immunol. Immunopathol.*, 45:17-28 (1987)). In contrast, macrophages in acutely inflamed tissues may express only MRP-14 (Delabie, J., et al., *Clin. Exp. Immunol.*, 81:123-126 (1990)). The expression of MRP-8 and MRP-14 by macrophages could be flecked exposure to tissue stimuli that either maintain expression or induce re-expression of the molecule (Palmer, D. G., et al., *Clin. Immunol. Immunopathol.*, 45:17-28 (1987)).

In common with other members of the S100 family, MRP-8 and MRP-14 are found predominately in a cytosolic location in both monocytes and neutrophils (Dale, I., et al., *Eur. J. Biochem.*, 134:1-6 (1983)). It is also possible that MRP-8 and MRP-14 can be expressed on the cell surface, although the majority of antibodies specific for these proteins do not react with circulating monocytes or neutrophils. There is also evidence that MRP-8 and MRP-14 exist extracellularly, however, neither protein has the signal peptide sequence for membrane translocation. Thus, MRP-8 and MRP-14 fall into the category of proteins, including interleukin-1 and basic fibroblast growth factor, that clearly have extracellular functions but about which little is known of their cellular release. Finally, MRP-8 and MRP-14 are found in the serum of patients with cystic fibrosis and other chronic inflammatory states such as rheumatoid arthritis and sarcoidosis (Bullock, S., et al., *Clin. Genet.*, 21:336-341 (1982)).

CP-10 is one of the most potent chemotactic proteins of the S100 family. An extracellular function of the murine CP-10 includes a potent chemotactic agent involved in phagocyte recruitment during inflammatory reactions (Lackman, M., et al., *J. Biol. Chem.*, 267:7499 (1992)). CP-10 has an apparent molecular weight of 10.3 kd and a complete sequence of 88 amino acids.

S100 proteins are characterized by two calcium binding regions, which are strongly conserved and are separated by an 8 to 12 amino acid hinge region (Kligman, D., *Trends Biochem. Sci.*, 13:437 (1988)). Although the hinge region length is conserved, the amino acid sequences are widely divergent. This divergence led to the hypothesis that the hinge region may concur functional specificity by interaction with the actor proteins (Id.).

BRIEF SUMMARY OF THE INVENTION

In accordance with one aspect of the present invention, there are provided novel polypeptides as well as biologically active and diagnostically or therapeutically useful fragments, analogs and derivatives thereof.

In accordance with another aspect of the present invention, there are provided isolated nucleic acid molecules encoding such polypeptides, including mRNAs, cDNAs, genomic DNA as well as biologically active and diagnostically or therapeutically useful fragments, analogs and derivatives thereof.

In accordance with another aspect of the present invention there is provided an isolated nucleic acid molecule encoding a mature polypeptide expressed by the DNA contained in ATCC Deposit No. 97304.

In accordance with another aspect of the present invention there are provided nucleic acid probes comprising nucleic acid molecules of sufficient length to specifically hybridize to sequences of the present invention.

In accordance with yet a further aspect of the present invention, there is provided a process for producing such polypeptides by recombinant techniques which comprises culturing recombinant prokaryotic and/or eukaryotic host cells, containing a nucleic acid sequence of the present invention, under conditions promoting expression of said protein and subsequent recovery of said protein.

In accordance with yet a further aspect of the present invention, there is provided a process for utilizing such polypeptides, or polynucleotides encoding such polypeptides for therapeutic purposes, for example, to treat tumors, chronic infections, leukemia, T-cell mediated auto-immune diseases, parasitic infections, psoriasis, asthma, allergy, to regulate hematopoiesis, to stimulate growth factor activity, to inhibit angiogenesis and to promote wound healing, to treat inflammatory disorders, to control cellular immune reactions, to treat malignant diseases, to inhibit casein kinase activity and to treat artherosclerosis.

In accordance with yet a further aspect of the present invention, there are provided antibodies against such polypeptides and a method of employing such antibodies to detect diseases related to an overexpression of the polypeptide of the present invention.

In accordance with yet another aspect of the present invention, there are provided antagonists to such polypeptides, which may be used to inhibit the action of such polypeptides, for example, in the treatment of certain auto-immune diseases, atherosclerosis, chronic inflammatory and infectious diseases, histamine and IgE-mediated allergic reactions, prostaglandin-independent fever, bone marrow failure, cancers, silicosis, sarcoidosis, rheumatoid arthritis, shock, hyper-eosinophilic syndrome and fibrosis in the asthmatic lung, cystic fibrosis, malignant diseases, psoriasis, diapedesis and urinary and kidney stones.

In accordance with another aspect of the present invention there is provided a method of diagnosing a disease or a susceptibility to a disease related to a mutation in the nucleic acid sequences and the protein encoded by such nucleic acid sequences.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings rein.

BRIEF DESCRIPTION OF THE DRAWINGS

The following drawings are illustrative of embodiments of the invention and are not meant to limit the scope of the invention as encompassed by the claims.

FIG. 1 displays the cDNA sequence SEQ ID NO:1 and corresponding deduced amino acid sequence SEQ ID NO:2 of the chemotactic cytokine I polypeptide of the present invention. The standard one-letter abbreviations for amino acids are used. Sequencing was performed using a 373 Automated DNA sequencer (Applied Biosystems, Inc.).

FIG. 2 is an illustration of amino acid sequence homology between the polypeptide of the present invention and pig calgranulin C protein (SEQ ID NO:9).

DETAILED DESCRIPTION OF THE INVENTION

Figure 3:
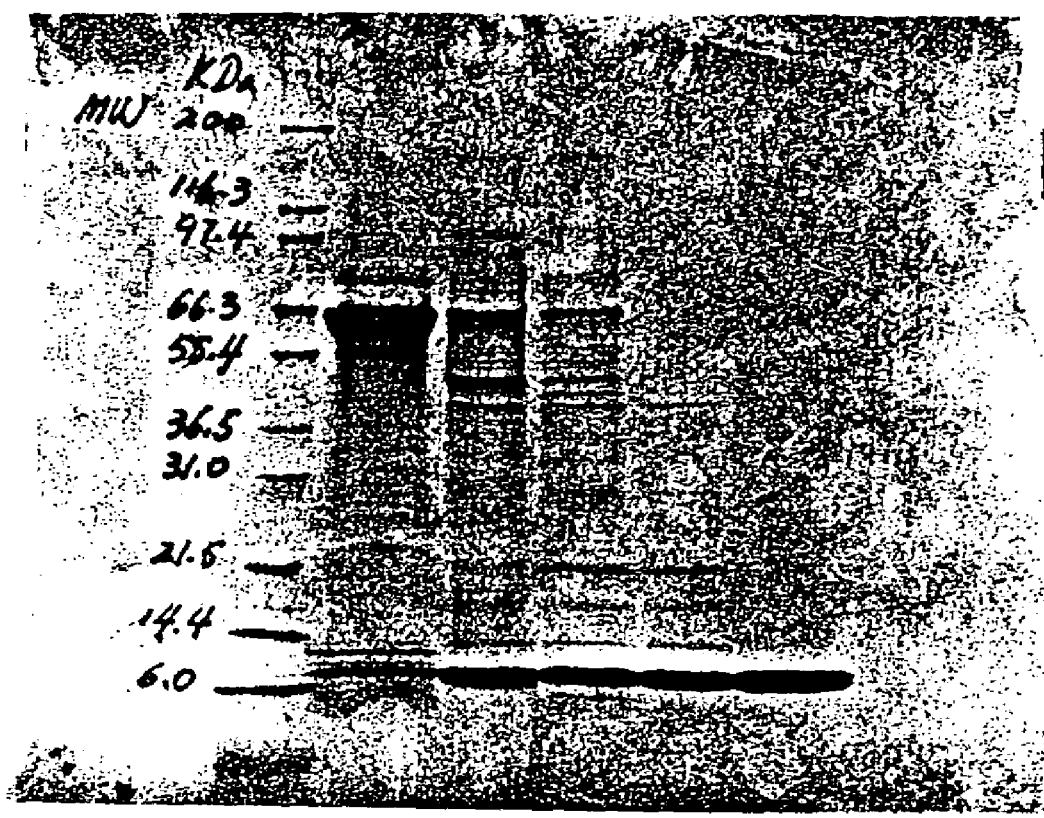
FIG. 3 shows structural and functional features of the polypeptide of the present invention deduced by the indicated techniques, as a function of amino acid sequence.

In accordance with an aspect of the present invention, there are provided isolated nucleic acids (polynucleotides) which encode for the mature polypeptides having the deduced amino acid sequences of FIG. 1 (SEQ ID No. 2).

Polynucleotides encoding the polypeptide of the present invention have been isolated from a human adult liver cDNA library. The polypeptide contains an open reading frame encoding a protein of 92 amino acids. The protein exhibits the highest degree of homology at the amino acid level to human MRP-14 with 46.739% identity and 67.391% similarity. The protein exhibits the highest degree of homology at the nucleotide level to SP100 protein with 56% identity and 56% similarity.

As seen in FIG. 2 the polypeptide of the present invention retains the calcium binding motifs present in all S100 protein members. For instance, amino acids, leucine and glutamine in amino acid position 4 and 5, the leucine at position 8, and the leucine and lyseine at position 28 and 30 are important for calcium binding activity and are shown to be preserved in the polypeptide of the present invention.

In accordance with another aspect of the present invention there are provided isolated polynucleotides encoding a mature polypeptide expressed by the DNA contained in ATCC Deposit No. 97304, deposited with the American Type Culture Collection, 10801 University Boulevard, Manassas, Va. 20110-2209, USA, on Sep. 25, 1995. The deposited material is a pBluescript SK (−) plasmid (Stratagene, LaJolla, Calif.) which contains the full-length chemotactic cytokine I cDNA cloned into the EcoRI, XhoI site.

The deposit(s) have been made under the terms of the Budapest Treaty on the International Recognition of the Deposit of Micro-organisms for purposes of Patent Procedure. The strain will be irrevocably and without restriction or condition released to the public upon the issuance of a patent. These deposits are provided merely as convenience to those of skill in the art and are not an admission that a deposit is required under 3.5 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptides may be identical to the coding sequences shown in FIG. 1 (SEQ ID NO:1) or may be a different coding sequence which coding sequence, as a result of the redundancy or degeneracy of the genetic code, encodes the same mature polypeptides as the DNA of FIG. 1 (SEQ ID NO:1).

The polynucleotides which encode for the mature polypeptides of FIG. 1 (SEQ ID NO:2) may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptides.

Thus, the term "polynucleotide encoding a polypeptide" encompasses a polynucleotide which includes coding sequence for the polypeptide and may also include additional coding and/or non-coding sequence such as introns.

The present invention further relates to variants of the hereinabove described polynucleotides which encode for fragments, analogs and derivatives of the polypeptide having the deduced amino acid sequences of FIG. 1 (SEQ ID NO:2). The variant of the polynucleotides may be a naturally occurring allelic variant of the polynucleotides or a non-naturally occurring variant of the polynucleotides.

Further particularly preferred in this regard are polynucleotides encoding human chemotactic cytokine I variants, analogs, derivatives and fragments, and variants, analogs and derivatives of the fragments, which have the amino acid sequence of the polypeptide of FIG. 1 or of the deposit in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the human chemotactic cytokine I. Also especially preferred in this regard are conservative substitutions. Most highly preferred are polypeptides having the amino acid sequence of FIG. 1 or of the deposit, without substitutions.

Thus, the present invention includes polynucleotides encoding the same mature polypeptides as shown in FIG. 1 (SEQ ID NO:2) as well as variants of such polynucleotides which variants encode for a fragment, derivative or analog of the polypeptides of FIG. 1 (SEQ ID NO:2). Such nucleotide variants include deletion variants, substitution variants and addition or insertion variants.

As hereinabove indicated, the polynucleotides may have a coding sequence which is a naturally occurring allelic variant of the coding sequences shown in FIG. 1 (SEQ ID NO:1). As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptides may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotides of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptides of the present invention. The marker sequence may be a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNA of FIG. 1 (SEQ ID NO:2).

Alternatively, the polynucleotide may have at least 20 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 and polynucleotides complementary thereto as well as portions thereof, which portions have at least 30 consecutive bases and preferably at least 50 consecutive bases and to polypeptides encoded by such polynucleotides.

The present invention further relates to polypeptides which have the deduced amino acid sequences of FIG. 1 (SEQ ID NO:2), as well as fragments, analogs and derivatives of such polypeptides.

The terms "fragment," "derivative" and "analog" when referring to the polypeptides of FIG. 1 (SEQ ID NO:2), means polypeptides which retain essentially the same biological function or activity as such polypeptides. Thus, an analog includes a proprotein which can be activated by cleavage of the proprotein portion to produce an active mature polypeptide.

Among the particularly preferred embodiments of the invention in this regard are polypeptides having the amino acid sequence of FIG. 1, variants, analogs, derivatives and fragments thereof, and variants, analogs and derivatives of the fragments. Alternatively, particularly preferred embodiments of the invention in this regard are polypeptides having the amino acid sequence of the human chemotactic cytokine I of the cDNA in the deposited clone, variants, analogs, derivatives and fragments thereof, and variants, analogs and derivatives of the fragments.

Further particularly preferred in this regard are variants, analogs, derivatives and fragments, and variants, analogs and derivatives of the fragments, having the amino acid sequence of the polypeptide of FIG. 1 or of the cDNA in the deposited clone, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of human chemotactic cytokine I. Also especially preferred in this regard are conservative substitutions. Most highly preferred are polypeptides having the amino acid sequence of FIG. 1 or the deposited clone without substitutions.

The polypeptides of the present invention may be recombinant polypeptides, natural polypeptides or synthetic polypeptides, preferably recombinant polypeptides.

The fragment, derivative or analog of the polypeptides of FIG. 1 (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2, and which have at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia). Eukaryotic: pWL-NEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene products encoded by the recombinant sequences. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa, 293 and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics to human disease.

The human chemotactic cytokine I polypeptides may be employed to inhibit bone marrow stem cell colony formation as adjunct protective treatment during cancer chemotherapy and for leukemia.

The human chemotactic cytokine I polypeptides may also be employed to inhibit epidermal keratinocyte proliferation for treatment of psoriasis, which is characterized by keratinocyte hyper-proliferation.

The human chemotactic cytokine I polypeptides may also be employed to treat solid tumors by stimulating the invasion and activation of host defense cells, e.g., cytotoxic T cells and macrophages and by inhibiting the angiogenesis of tumors. They may also be employed to enhance host defenses against resistant chronic and acute infections, for example, mycobacterial infections via the attraction and activation of microbicidal leukocytes.

The human chemotactic cytokine I polypeptides may also be employed to inhibit T cell proliferation by the inhibition of IL-2 biosynthesis for the treatment of T-cell mediated autoimmune diseases and lymphocytic leukemias.

The chemotactic cytokine I polypeptides may also be employed to stimulate wound healing, both via the recruitment of debris clearing and connective tissue promoting inflammatory cells and also via its control of excessive TGFβ-mediated fibrosis. In this same manner, 1 may also be employed to treat other fibrotic disorders, including liver cirrhosis, osteoarthritis and pulmonary fibrosis.

The human chemotactic cytoKine I polypeptides of the present invention may also be employed as cytostatic agents for antibacterial and antimicrobial functions.

They may also be employed to regulate hematopoiesis, by regulating the activation and differentiation of various hematopoietic progenitor cells, for example, to release mature leukocytes from the bone marrow following chemotherapy.

The polynucleotides and polypeptides encoded by such polynucleotides may also be utilized for in vitro purposes related to scientific research, synthesis of DNA and manufacture of DNA vectors and for designing therapeutics and diagnostics for the treatment of human disease.

The polypeptides of the present invention and fragments and analogs and derivatives thereof may be identified by assays which detect chemotactic activity. One example of such an assay comprises testing such polypeptide for chemotactic activities toward murine polymorphonuclear cells or macrophages, human PMN (isolated on mono-poly-resolving medium; FLOW, McLean, Va.). Conditioned medium (diluted and fully supplemented Dulbecco's Modified Eagles medium) and cell lysates (diluted and supplemented Dulbecco's Modified Eagles medium containing 0.1% BSA instead of 10% FCS) from transiently transfected CV-1 cells are tested for chemotactic activities toward murine PMNs. Endotoxin content of media and all solutions to be tested are measured using a chromogenic limulus amoebocyte lysate assay (Cape Cod Associates, Woods Hole, Mass.), which was sensitive to 5 pg endotoxin/ml. Chemotactic activity is defined as the mean number of cells migrating through the pores of the membrane in 3 to 5 standard fields and quantitated by image analysis (Wild-Leitz, Rockly, N.J.) using planimetry measurements (magnification times 100) or by counting normally. Endotoxin-activated mouse serum (50%) or FMLP ($10^{-7}$M) are used as positive controls.

This invention is also related to the use of the chemotactic cytokine I polypeptide gene as part of a diagnostic assay for detecting diseases or susceptibility to diseases related to the presence of mutations in the chemotactic cytokine I polypeptide nucleic acid sequences. Such diseases are related to under-expression of the human chemokine polypeptides, for example, tumors and cancers.

Individuals carrying mutations in the chemotactic cytokine I polypeptide gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163-166 (1986)) prior to analysis. RNA or cDNA may also be used for the same purpose. As an example, PCR primers complementary to the nucleic acid encoding chemotactic cytokine I polypeptide can be used to identify and analyze chemotactic cytokine I polypeptide mutations. For example, deletions and insertions can be detected by a change in size of the amplified product in comparison to the normal genotype. Point mutations can be identified by hybridizing amplified DNA to radiolabeled chemotactic cytokine I polypeptide RNA or alternatively, radiolabeled chemotactic cytokine I polypeptide antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397-4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of chemotactic cytokine I polypeptide in various tissues since an over-expression of the proteins compared to normal control tissue samples may detect the presence of a disease or susceptibility to a disease, for example, cystic fibrosis or malignancies such as cancers and tumors. Assays used to detect levels of chemotactic cytokine I polypeptide in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the chemotactic cytokine I polypeptide antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any chemotactic cytokine I polypeptide attached to the polystyrene dish. All unbound monoclonal antibody is washed out with buffer. The reporter antibody linked to horseradish peroxidase is now placed in the dish resulting in binding of the reporter antibody to any monoclonal antibody bound to chemotactic cytokine I polypeptide. Unattached reporter antibody is then washed out. Peroxidase substrates are then added to the dish and the amount of color developed in a given time period is a measurement of the amount of chemotactic cytokine I polypeptide present in a given volume of patient sample when compared against a standard curve.

A competition assay may be employed wherein antibodies specific to chemotactic cytokine I polypeptide are attached to a solid support and labeled chemotactic cytokine I polypeptide and a sample derived from the host are passed over the solid support and the amount of label detected, for example by liquid scintillation chromatography, can be correlated to a quantity of chemotactic cytokine I polypeptide in the sample.

A "sandwich" assay is similar to an ELISA assay. In a "sandwich" assay chemotactic cytokine I polypeptide is passed over a solid support and binds to antibody attached to a solid support. A second antibody is then bound to the chemotactic cytokine I polypeptide. A third antibody which is labeled and specific to the second antibody is then passed over the solid support and binds to the second antibody and an amount can then be quantified.

This invention provides a method for identification of the receptors for the human chemotactic cytokine I polypeptides. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

This invention provides a method of screening compounds to identify agonists and antagonists to the human chemotactic cytokine I polypeptides of the present invention. An agonist is a compound which has similar biological functions of the polypeptides, while antagonists block such functions. Antagonists and agonists may be identified by the chemotaxis assay described above.

Examples of potential chemotactic cytokine I polypeptide antagonists include antibodies, or in some cases, oligonucleotides, which bind to the polypeptides. Another example of a potential antagonist is a negative dominant mutant of the polypeptides. Negative dominant mutants are polypeptides which bind to the receptor of the wild-type polypeptide, but fail to retain biological activity.

Antisense constructs prepared using antisense technology are also potential antagonists. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple-helix, see Lee et al., Nucl. Acids Res., 6:3073 (1979); Cooney et al, Science, 241:456 (1988); and Dervan et al., Science, 251: 1360 (1991)), thereby preventing transcription and the production of the human chemotactic cytokine. The antisense RNA oligonucleotide hybridizes to the mRNA in vivo and blocks translation of the mRNA molecule into the polypeptides (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the human chemotactic cytokines.

Another potential human chemotactic cytokine I antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but are not limited to, small peptides or peptide-like molecules.

The antagonists may be employed to inhibit the chemotaxis and activation of macrophages and their precursors, and of neutrophils, basophils, B lymphocytes and some T cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes.

The antagonists may also be employed to treat infectious diseases including silicosis, sarcoidosis, idiopathic pulmonary fibrosis by preventing the recruitment and activation of mononuclear phagocytes. They may also be employed to treat idiopathic hyper-eosinophilic syndrome by preventing eosinophil production and migration. Endotoxic shock may also be treated by the antagonists by preventing the migration of macrophages and their production of the human chemotactic cytokines of the present invention.

The antagonists may also be employed for treating atherosclerosis, by preventing monocyte infiltration in the artery wall.

The antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated.

The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. In addition, the antagonists may be employed to treat inflammatory lesions, e.g., rheumatoid arthritis, sarcoid and catscratch granulomas, and dermathopathic lymphadenopathy.

Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies.

The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by chemokines.

The antagonists may also be employed to treat cases of bone marrow failure, for example, aplastic anemia and myelodysplastic syndrome.

The antagonists may also be employed to treat asthma and allergy by preventing eosinophil accumulation in the lung. The antagonists may also be employed to treat subepithelial basement membrane fibrosis which is a prominent feature of the asthmatic lung.

Antagonists may also be employed to treat psoriasis since an elevated level of members of the S100 protein family have been found in the epidermis of psoriatic models.

The antagonists may be employed in a composition with a pharmaceutically acceptable carrier, e.g., as hereinafter described.

The human chemotactic cytokines and agonists and antagonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides and agonists and antagonists may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the polypeptides will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The human chemotactic cytokines, and agonists or antagonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5-14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells. The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

Antibodies specific to the polypeptide of the present invention may be employed as a diagnostic to determine elevated levels of the polypeptide in a sample derived from a host by techniques known in the art. These elevated levels are indicative of certain disorders which are characterized by elevated levels of the protein of the present invention and members of its family, for example, lichen planus, lupus erythematosus and psoriasis vulgaris, cystic fibrosis and inflammatory lesions, e.g., rheumatoid arthritis, sarcoid and catscratch granulomas and dermathopathic lymphadenopathy.

For preparation of monoclonal antibodies, any technique which provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456-457 (1973).

EXAMPLE 1

Bacterial Expression and Purification of Chemotactic Cytokine

The DNA sequence encoding for chemotactic cytokine, ATCC # 97304, was initially amplified using PCR oligonucleotide primers corresponding to the 5' and 3' end sequences of the processed chemotactic cytokine I nucleic acid sequence (minus the putative signal peptide sequence). Additional nucleotides corresponding to the chemotactic cytokine I gene were added to the 5' and 3' end sequences respectively. The 5' oligonucleotide primer has the sequence 5' CGC GGA TCC ATGACAAACTTG 3' (SEQ ID NO:3) contains a BamHI restriction enzyme site (bold) followed by 13 nucleotides of chemotactic cytokine I coding sequence (underlined). The 3' sequence 5' CGC GGA TCC CTA CTC TTT GTG GGT GTG G 3' (SEQ ID NO:4) contains complementary sequences to a BamHI site (bold) and was followed by 16 nucleotides of gene specific sequences preceding the termination codon. The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with BamHI. The coding sequence was amplified using the described primers (SEQ ID NO:3 and 4) and then digested with BamHI. The digested sequences were ligated into pQE-9 and were inserted in frame with the sequence encoding for the histidine tag and the RBS. The ligation mixture was then used to transform the E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl pH 8.0. After clarification, solubilized chemotactic cytokine I was purified from this solution by chromatography on a Nickel-Chelate column (Hochuli, E. et al., J. Chromatography 411:177-184 (1984)) under conditions that allow for tight binding by proteins containing the 6-His tag. Chemotactic cytokine I (>90% pure) was eluted from the column in 6M guanidine HCl. Protein renaturation out of GnHCl can be accomplished by several protocols (Jaenicke, R. and Rudolph, R., Protein Structure—A Practical Approach, IRL Press, New York (1990)). Initially, step dialysis was utilized to remove the GnHCL. Alternatively, the purified protein isolated from the Ni-chelate column can be bound to a second column over which a decreasing linear GnHCL gradient was run. The protein was allowed to renature while bound to the column and was subsequently eluted with a buffer containing 250 mM Imidazole, 150 mM NaCl, 25 mM Tris-HCl pH 7.5 and 10% Glycerol. Finally, soluble protein was dialyzed against a storage buffer containing 5 mM Ammonium Bicarbonate.

EXAMPLE 2

Expression of Recombinant Chemotactic Cytokine I in COS Cells

The expression of plasmid, chemotactic cytokine I HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire chemotactic cytokine I precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding for chemotactic cytokine, ATCC # 97304, is constructed by PCR using two primers: the 5' primer 5' GCGCGGATCCACC ATGACAAAACTTGAAGAG 3' (SEQ ID NO:5) contains a BamHI site (in bold) followed by 15 nucleotides of chemotactic cytokine I coding sequence starting from the minus 3 position relative to initiation codon; the 3' sequence 5' GCGCTCTAGATCAAGCGTAGTCTGG-GACGTCGTATGGGTACTCTTTG TGGGTGTG 3' (SEQ ID NO:6) contains complementary sequences to an XbaI site, translation stop codon, HA tag and the last 15 nucleotides of the chemotactic cytokine I coding sequence (not including the stop codon). Therefore, the PCR product contains a BamHI site, chemotactic cytokine I coding sequence followed by HA tag fused in frame, a translation termination stop codon next to the HA tag, and an XbaI site. The PCR amplified DNA fragment and the vector, pcDNAI/Amp, are digested with BamHI and XbaI restriction enzyme and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant chemotactic cytokine, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the chemotactic cytokine I HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media are precipitated with a HA specific monoclonal antibody. Proteins precipitated are analyzed by SDS-PAGE.

EXAMPLE 3

Cloning and Expression of Chemotactic Cytokine I Using the Baculovirus Expression System The DNA sequence encoding the full length chemotactic cytokine I protein, ATCC # 97304, is amplified using PCR oligonucleotide primers corresponding to the 5' and 3' sequences of the gene:

The 5' primer has the sequence 5' CGC GGA TCC CAC AAA ACT TGA AGA GCA TC 3' (SEQ ID NO:7) and contains a BamHI restriction enzyme site (in bold) followed by 19 nucleotides of coding sequence.

The 3' primer has the sequence 5' CGC GGA TCC CTA CTC TTT GTG GGT GTG G 3' (SEQ ID NO:8) and contains the cleavage site for the restriction endonuclease BamHI and 16 nucleotides complementary to the 3' translated sequence of the chemotactic cytokine I gene and stop codon. The amplified sequences are isolated from a 1% agarose gel using a commercially available kit ("Geneclean," BIO 101 Inc., La Jolla, Calif.). The fragment is then digested with the endonucleases BamHI, then purified again on a 1% agarose gel. This fragment is designated F2.

The vector pA2-GP (modification of pVL941 vector, discussed below) is used for the expression of the chemotactic cytokine I protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases BamHI and Asp781. The polyadenylation site of the simian virus (SV)40 is used for efficient polyadenylation. For an easy selection of recombinant viruses the beta-galactosidaseqgene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pA2-GP such as pAc373, pVL941 if a signal peptide is added to the coding sequence as described (Luckow, V. A. and Summers, M. D., Virology, 170:31-39).

The plasmid is digested with the restriction enzymes BamHI and then dephosphorylated using calf intestinal phosphatase by procedures known in the art. The DNA is then isolated from a 10% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E. coli* HB101 cells are then transformed and bacteria identified that contained the plasmid (pBac-chemotactic cytokine) with the chemotactic cytokine I gene using the enzymes BamHI and Asp781. The sequence of the cloned fragment is confirmed by DNA sequencing.

5 μg of the plasmid pBac-chemotactic cytokine I is cotransfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413-7417 (1987)).

1 μg of BaculoGold™ virus DNA and 5 μg of the plasmid pBac-chemotactic cytokine I are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added dropwise to the Sf9 (*Spodoptera frugiperda*) insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9-10).

Four days after the serial dilution, the viruses are added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-chemotactic cytokine I at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours.

The growth medium was harvested on day 4 post-infection. After the removal of baculovirus cells by continuous centrifugation, the supernatant was applied to a cation exchange column (pros HS 50 resin from PerSeptive Biosystem) pre-equilibrated with buffer A (40 mM NaAcetate, 50 mM NaCl, pH 5.5). The column was eluted stepwise with increasing NaCl concentration in the same buffer. The fractions containing the human chemotactic cytokine I were pooled, diluted with buffer A and applied to another cation exchange column (CM20), followed by a NaCl gradient elution. The combined fractions were further purified by gel filtration chromatography (Superdex 200 or Superdex 75 from Pharmacia Biotech). Human chemotactic cytokine I was finally purified to homogeneity (95%) and concentrated by cation exchange chromatography (CM20) after the gel filtration fractionation.

EXAMPLE 4

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219-25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a nucleic acid sequence encoding at least 30 contiguous amino acid residues of SEQ ID NO:2.

2. The isolated polynucleotide of claim 1 comprising a nucleic acid sequence encoding at least 50 contiguous amino acid residues of SEQ ID NO:2.

3. The isolated polynucleotide of claim 2 comprising a nucleic acid sequence encoding amino acids 2 to 92 of SEQ ID NO:2.

4. An isolated polynucleotide comprising a nucleic acid sequence encoding amino acids 1 to 92 in SEQ ID NO:2.

5. An isolated polynucleotide comprising a nucleic acid sequence complementary to the polynucleotide of claim 1.

6. The isolated polynucleotide of claim 1 which is DNA.

7. The isolated polynucleotide of claim 1 further comprising a heterologous nucleic acid sequence.

8. An isolated polynucleotide comprising a nucleic acid sequence encoding at least 30 contiguous amino acid residues of the polypeptide encoded by the human cDNA contained in ATCC Deposit No. 97304.

9. The isolated polynucleotide of claim 8 comprising a nucleic acid sequence encoding at least 50 contiguous amino acid residues of the polypeptide encoded by the human cDNA contained in ATCC Deposit No. 97304.

10. The isolated polynucleotide of claim 9 comprising a nucleic acid sequence encoding the polypeptide encoded by the full-length human cDNA contained in ATCC Deposit No. 97304.

11. An isolated polynucleotide comprising a nucleic acid sequence complementary to the polynucleotide of claim 8.

12. The isolated polynucleotide of claim 8 which is DNA.

13. The isolated polynucleotide of claim 8 further comprising a heterologous nucleic acid sequence.

14. A vector comprising the polynucleotide of claim 1.

15. A vector comprising the polynucleotide of claim 2.

16. A vector comprising the polynucleotide of claim 3.

17. A vector comprising the polynucleotide of claim 4.

18. A vector comprising the polynucleotide of claim 8.

19. A vector comprising the polynucleotide of claim 9.

20. A vector comprising the polynucleotide of claim 10.

21. An isolated host cell comprising the polynucleotide of claim 1 operably linked to a heterologous regulatory sequence which controls gene expression.

22. An isolated host cell comprising the polynucleotide of claim 2 operably linked to a heterologous regulatory sequence which controls gene expression.

23. An isolated host cell comprising the polynucleotide of claim 3 operably linked to a heterologous regulatory sequence which controls gene expression.

24. An isolated host cell comprising the polynucleotide of claim 4 operably linked to a heterologous regulatory sequence which controls gene expression.

25. An isolated host cell comprising the polynucleotide of claim 8 operably linked to a heterologous regulatory sequence which controls gene expression.

26. An isolated host cell comprising the polynucleotide of claim 9 operably linked to a heterologous regulatory sequence which controls gene expression.

27. An isolated host cell comprising the polynucleotide of claim 10 operably linked to a heterologous regulatory sequence which controls gene expression.

28. A process for producing a polypeptide comprising culturing the host cell of claim 21 under conditions resulting in expression of the encoded polypeptide and recovering said polypeptide.

29. A process for producing a polypeptide comprising culturing the host cell of claim 22 under conditions resulting in expression of the encoded polypeptide and recovering said polypeptide.

30. A process for producing a polypeptide comprising culturing the host cell of claim 23 under conditions resulting in expression of the encoded polypeptide and recovering said polypeptide.

31. A process for producing a polypeptide comprising culturing the host cell of claim 24 under conditions resulting in expression of the encoded polypeptide and recovering said polypeptide.

32. A process for producing a polypeptide comprising culturing the host cell of claim 25 under conditions resulting in expression of the encoded polypeptide and recovering said polypeptide.

33. A process for producing a polypeptide comprising culturing the host cell of claim 26 under conditions resulting in expression of the encoded polypeptide and recovering said polypeptide.

34. A process for producing a polypeptide comprising culturing the host cell of claim 27 under conditions resulting in expression of the encoded polypeptide and recovering said polypeptide.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 480 BASE PAIRS
      (B) TYPE: NUCLEIC ACID
      (C) STRANDEDNESS: SINGLE
      (D) TOPOLOGY: LINEAR (ii) MOLECULE TYPE: cDNA (xi) SEQUENCE DESCRIPTION: SEQ ID NO:1:

```
CACGAGCACC ACTGCTGGCT TTTTGCTGTA GCTCCACATT CCTGTGCATT GAGGGGTTAA    60

CATTAGGCTG GGAAGATGAC AAAACTTGAA GAGCATCTGG AGGGAATTGT CAATATCTTC   120

CACCAATACT CAGTTCGGAA GGGGCATTTT GACACCCTCT CTAAGGGTGA GCTGAAGCAG   180

CTGCTTACAA AGGAGCTTGC AAACACCATC AAGAATATCA AGATAAAGC TGTCATTGAT    240

GAAATATTCC AAGGCCTGGA TGCTAATCAA GATGAACAGG TCGACTTTCA AGAATTCATA   300

TCCCTGGTAG CCATTGCGCT GAAGGCTGCC CATTACCACA CCCACAAAGA GTAGGTAGCT   360

CTCTGAAGGC TTTTTACCCA GCAATGTCCT CAATGGAGGG GTCTTTTCTT TGCCTCACCA   420

AAACCCAGCT TGACCCCTGG GGGGAGTTAA GAGTTAATAA CCACACTTAC GGAAAGTTCT   480
```

(2) INFORMATION FOR SEQ ID NO:2:

(i) SEQUENCE CHARACTERISTICS:
      (A) LENGTH: 92 AMINO ACIDS
      (B) TYPE: AMINO ACID
      (C) STRANDEDNESS:
      (D) TOPOLOGY: LINEAR (ii) MOLECULE TYPE: PROTEIN (xi) SEQUENCE DESCRIPTION: SEQ ID NO:2:

```
Met Thr Lys Leu Glu Glu His Leu Glu Gly Ile Val Asn Ile Phe
                5                  10                  15

His Gln Tyr Ser Val Arg Lys Gly His Phe Asp Thr Leu Ser Lys
                20                 25                  30

Gly Glu Leu Lys Gln Leu Leu Thr Lys Glu Leu Ala Asn Thr Ile
                35                 40                  45

Lys Asn Ile Lys Asp Lys Ala Val Ile Asp Glu Ile Phe Gln Gly
                50                 55                  60

Leu Asp Ala Asn Gln Asp Glu Gln Val Asp Phe Gln Glu Phe Ile
                65                 70                  75

Ser Leu Val Ala Ile Ala Leu Lys Ala Ala His Tyr His Thr His
                70                 85                  90

Lys Glu
```

(2) INFORMATION FOR SEQ ID NO:3:

(i) SEQUENCE CHARACTERISTICS:
      (A) LENGTH: 22 BASE PAIRS
      (B) TYPE: NUCLEIC ACID
      (C) STRANDEDNESS: SINGLE
      (D) TOPOLOGY: LINEAR (ii) MOLECULE TYPE: cDNA (xi) SEQUENCE DESCRIPTION: SEQ ID NO:3:

CGCGGATCCA TGACAAAACT TG                                                22

(2) INFORMATION FOR SEQ ID NO:4:

(i) SEQUENCE CHARACTERISTICS:
             (A) LENGTH: 28 BASE PAIRS
             (B) TYPE: NUCLEIC ACID
             (C) STRANDEDNESS: SINGLE
             (D) TOPOLOGY: LINEAR (ii) MOLECULE TYPE: Oligonucleotide (xi) SEQUENCE DESCRIPTION: SEQ ID NO:4:

CGCGGATCCC TACTCTTTGT GGGTGTGG                                          28

(2) INFORMATION FOR SEQ ID NO:5:

(i) SEQUENCE CHARACTERISTICS:
             (A) LENGTH: 31 BASE PAIRS
             (B) TYPE: NUCLEIC ACID
             (C) STRANDEDNESS: SINGLE
             (D) TOPOLOGY: LINEAR (ii) MOLECULE TYPE: Oligonucleotide (xi) SEQUENCE DESCRIPTION: SEQ ID NO:5:

GCGCGGATCC ACCATGACAA AACTTGAAGA G                                      31

(2) INFORMATION FOR SEQ ID NO:6:

(i) SEQUENCE CHARACTERISTICS:
             (A) LENGTH: 55 BASE PAIRS
             (B) TYPE: NUCLEIC ACID
             (C) STRANDEDNESS: SINGLE
             (D) TOPOLOGY: LINEAR (ii) MOLECULE TYPE: Oligonucleotide (xi) SEQUENCE DESCRIPTION: SEQ ID NO:6:

GCGCTCTAGA TCAAGCGTAG TCTGGGACGT CGTATGGGTA CTCTTTGTGG GTGTG            55

(2) INFORMATION FOR SEQ ID NO:7:

(i) SEQUENCE CHARACTERISTICS:
             (A) LENGTH: 29 BASE PAIRS
             (B) TYPE: NUCLEIC ACID
             (C) STRANDEDNESS: SINGLE
             (D) TOPOLOGY: LINEAR (ii) MOLECULE TYPE: Oligonucleotide (xi) SEQUENCE DESCRIPTION: SEQ ID NO:7:

CGCGGATCCC ACAAAACTTG AAGAGCATC                                         29

(2) INFORMATION FOR SEQ ID NO:8:

(i) SEQUENCE CHARACTERISTICS:
             (A) LENGTH: 28 BASE PAIRS
             (B) TYPE: NUCLEIC ACID
             (C) STRANDEDNESS: SINGLE
             (D) TOPOLOGY: LINEAR (ii) MOLECULE TYPE: Oligonucleotide (xi) SEQUENCE DESCRIPTION: SEQ ID NO:8:

CGCGGATCCC TACTCTTTGT GGGTGTGG                                          28

-continued (2) INFORMATION FOR SEQ ID NO:9:

(i) SEQUENCE CHARACTERISTICS:
        (A) LENGTH: 91 AMINO ACIDS
        (B) TYPE: AMINO ACID
        (C) STRANDEDNESS:
        (D) TOPOLOGY: LINEAR (ii) MOLECULE TYPE: PEPTIDE (xi) SEQUENCE DESCRIPTION: SEQ ID NO:9:

Thr Lys Leu Glu Asp His Leu Glu Gly Ile Ile Asn Ile Phe His
                 5                  10                  15

Gln Tyr Ser Val Arg Leu Gly His Tyr Asp Thr Leu Ile Lys Arg
                20                  25                  30

Glu Leu Lys Gln Leu Ile Tyr Lys Glu Leu Pro Asn Thr Leu Lys
                35                  40                  45

Asn Thr Lys Asp Gln Gly Thr Ile Asp Lys Ile Phe Gln Asn Leu
                50                  55                  60

Asn Ala Asn Gln Asp Glu Gln Val Ser Phe Lys Glu PHe Val Val
                65                  70                  75

Leu Val Thr Asp Val Leu Ile Thr Ala His Asp Asn Ile His Lys
                70                  85                  90

Glu (2) INFORMATION FOR SEQ ID NO:10:

(i) SEQUENCE CHARACTERISTICS:
        (A) LENGTH: 100 AMINO ACIDS
        (B) TYPE: AMINO ACID
        (C) STRANDEDNESS:
        (D) TOPOLOGY: LINEAR (ii) MOLECULE TYPE: PEPTIDE (xi) SEQUENCE DESCRIPTION: SEQ ID NO:10:

Met Thr Cys Lys Met Ser Gln Leu Glu Arg Asn Ile Glu Thr Ile
                 5                  10                  15

Ile Asn Thr Phe His Gln Tyr Ser Val Lys Leu Gly His Pro Asp
                20                  25                  30

Thr Leu Asn Gln Gly Glu Phe Lys Glu Leu Val Arg Lys Asp Leu
                35                  40                  45

Gln Asn Phe Leu Lys Lys Glu Asn Lys Asn Glu Lys Val Ile Glu
                50                  55                  60

His Ile Met Glu Asp Leu Asp Thr Asn Ala Asp Lys Gln Leu Ser
                65                  70                  75

Phe Glu Glu Phe Ile Met Leu Met Ala Arg Leu Thr Trp Ala Ser
                70                  85                  90

His Glu Lys Met His Glu Gly Asp Glu Gly
                95                 100